United States Patent
Banks et al.

[11] Patent Number: 5,965,076
[45] Date of Patent: Oct. 12, 1999

[54] METHOD FOR FABRICATING SOFT TISSUE IMPLANTS WITH MICROSCOPIC SURFACE ROUGHNESS

[75] Inventors: Bruce A. Banks, Olmsted Township; Sharon K. Rutledge, Bedford, both of Ohio

[73] Assignee: The United States of America as represented by the Administrator of the National Aeronautics and Space Administration, Washington, D.C.

[21] Appl. No.: 08/936,492

[22] Filed: Sep. 22, 1997

[51] Int. Cl.⁶ .............................. B29C 33/40; B05D 1/12; B05D 1/32
[52] U.S. Cl. .................... 264/219; 264/447; 264/446; 156/276; 156/344; 425/2; 427/133; 427/180; 427/259; 427/264; 427/551; 427/552
[58] Field of Search .................... 264/219, 447, 264/446; 156/276, 344; 427/551, 552, 180, 259, 264, 270, 133; 425/2

[56] References Cited

U.S. PATENT DOCUMENTS

| | | |
|---|---|---|
| 3,905,047 | 9/1975 | Long . |
| 4,315,782 | 2/1982 | Tarng ........................................ 148/1.5 |
| 4,352,835 | 10/1982 | Holbrook et al. ........................ 427/38 |
| 4,888,203 | 12/1989 | Rothschild et al. .................... 427/53.4 |
| 4,955,909 | 9/1990 | Ersek et al. . |
| 4,960,425 | 10/1990 | Yan et al. . |
| 4,969,906 | 11/1990 | Kronman . |
| 5,002,572 | 3/1991 | Picha . |
| 5,227,602 | 7/1993 | Kuhn . |
| 5,263,986 | 11/1993 | Noiles et al. . |
| 5,489,410 | 2/1996 | Baumgartner et al. ................. 264/219 |

Primary Examiner—Catherine Timm
Assistant Examiner—Suzanne E. Mason
Attorney, Agent, or Firm—Kent N. Stone

[57] ABSTRACT

A method for fabricating soft tissue implants using a mold. The cavity surface of an initially untextured mold, made of an organic material such as epoxy, is given a thin film coating of material that has pinholes and is resistant to atomic particle bombardment. The mold cavity surface is then subjected to atomic particle bombardment, such as when placed in an isotropic atomic oxygen environment. Microscopic depressions in the mold cavity surface are created at the pinhole sites on the thin film coating. The thin film coating is removed and the mold is then used to cast the soft tissue implant. The thin film coating having pinholes may be created by chilling the mold below the dew point such that water vapor condenses upon it; distributing particles, that can partially dissolve and become attached to the mold cavity surface, onto the mold cavity surface; removing the layer of condensate, such as by evaporation; applying the thin film coating over the entire mold surface; and, finally removing the particles, such as by dissolving or brushing it off. Pinholes are created in the thin film coating at the sites previously occupied by the particles.

30 Claims, 2 Drawing Sheets

5,965,076

METHOD FOR FABRICATING SOFT TISSUE IMPLANTS WITH MICROSCOPIC SURFACE ROUGHNESS

ORIGIN OF THE INVENTION

The invention described herein was made in the performance of work done by employees of the U.S. Government and may be manufactured and used by or for the government for governmental purposes without the payment of any royalties thereon or therefore.

BACKGROUND OF THE INVENTION

1. Field of the Invention

The invention relates in general to implantable medical devices, and specifically to a process for fabricating soft tissue elastomeric implants having surface roughness.

2. Description of the Related Art

Current medical technology has recognized the benefits of a textured surface morphology on medical implants in producing non-classical tissue response to medical implants in the soft tissue (fascia, muscle, adipose, etc.) of a living body, such as a mammal, animal or human. The introduction of a foreign object into soft tissue produces a "classical" tissue response wherein a relatively thick, dense fibrous capsule or a layer of highly oriented collagen forms around the object. This fibrous encapsulation of implantable medical devices or surgical implants, such as prostheses, tissue expanders, breast or mammary prostheses or implants, mass transport or drug infusion devices, and sensors, leads to a common problem referred to as "capsule contracture." In capsule contracture, the fibrous capsule, over time, contracts and squeezes the implanted medical device. If the implanted device is soft and pliable, such as a human mammary implant, contracture causes the implant to deform and tighten, losing its natural shape and softness. Moreover, capsule contracture may also adversely affect the performance of an implanted mass transport device or sensor by inhibiting the diffusion of a therapeutic substance from the mass transport device or by inhibiting the flow of bodily fluid to the sensors. A textured surface with an array of small, closely spaced projections has been proven to reduce the amount of scar tissue, enhance the vascularization near an implant surface, interfere with long-range ordering of collagen, and improve the anchorage for the implant.

Various methods of producing textured surfaces with projections have been proposed. U.S. Pat. No. 4,955,909 to Ersek et al. discloses the texturing of an uncured silicone surface by thrusting selected molecules of a sufficient size and shape onto the surface with sufficient impact to alter the surface morphology prior to vulcanization of the silicone. U.S. Pat. No. 4,960,425 to Yan et al. discloses a similar procedure wherein textured screens with particular patterns are pressed upon the unvulcanized or partially vulcanized silicone shell on the implant before the silicone shell is cured. The use of textured screens with round perforations creates generally columnar projections. The use of textured screens with a crossed or knitted pattern creates projections or indentations of a regular geometric shape. In particular, Yan et al. teaches a preferred texturizing medium to be a reticulated foam which yields projections having irregular shapes when pressed upon the uncured silicone shell. U.S. Pat. No. 5,263,986 to Noiles et al. discloses the use of sintering or plasma spraying of particles onto the implant surface to create a rough surface morphology. U.S. Pat. No. 3,905,047 to Long discloses the use of selective surface etching, as by acid or the like, to create a rough surface texture. U.S. Pat. No. 5,227,602 to Kuhn teaches the use of a spark erosion process to form a dental prosthesis from a solid matrix body.

In summary, processes exist which alter the surface morphology of an implant by physically indenting the surface of an unvulcanized or partially vulcanized silicone outer shell of an implant prior to curing the silicone. Other processes include sintering particles to the surface; subjecting the surface to corrosive chemicals; and using electric sparks to form the prosthesis. Other physical techniques, well known in the industry, include laser etching, scratching, carving, burning, or the like, to cause a sufficient texturization of the surface.

The use of molds is also well known in the industry. Yan et al. teaches the use of injection molding to cast a textured silicone shell by using a textured mold. However, Yan et al. does not disclose how the mold was textured. U.S. Pat. No. 5,002,572 to Picha discloses the use of molding procedures to form micropillars on the implant surface. Picha further discloses that the mold may be textured by means of laser etching techniques, ion milling, or chemical etching, all well known in the art. Other methods well known in the art for texturing the mold include manual indentation of the surface of the mold and sputter texturing of fluoropolymer molds. However, these methods of texturing the mold require extensive manual efforts and are costly.

SUMMARY OF THE INVENTION

Accordingly, it is an object of the invention to provide a cost efficient process of fabricating soft tissue implants.

Another object of the invention is to provide a method for producing implant surfaces with a uniform distribution of small protrusions or bumps, without requiring labor intensive efforts to prepare the surface.

A further object of the invention is to provide a procedure whereby the shape, size, and spacing of projections can be readily controlled.

A further object of the invention is to maximize cost efficiency by providing a process which employs relatively inexpensive methods to produce bumps or cavities on implants, while employing relatively more expensive methods only to produce the molds which are used to produce the implants, and reusing the molds to produce multiple implants.

It is still a further object of the invention to provide a process wherein the implant surface can be optimally configured, such that improved implant fixation and improved tissue fibrous capsule response will result.

In order to achieve the foregoing and other objects, in accordance with the purposes of the present invention as described therein, a method for fabricating soft tissue implants having surface roughness from a mold comprises the steps of: coating the mold cavity surface with a thin film coating of material that has pinholes and is resistant to atomic particle bombardment; subjecting the mold cavity surface to atomic particle bombardment so that depressions are created in the mold cavity surface at the pinhole sites on the thin film coating; removing the thin film coating from the mold cavity surface; and creating an implant by using the mold to cast the implant. A thin film coating having pinholes may be created by: chilling the mold below the dew point such that water vapor condenses upon it; distributing particles, that can partially dissolve and become attached to the mold cavity surface, onto the mold cavity surface; removing the layer of condensate, such as by evaporation; applying the thin film coating over the entire mold surface;

and, finally removing the particles, such as by dissolving or brushing it off, thereby leaving pinholes in the thin film coating at the sites previously occupied by the particles.

The present invention can be used not only on flat surfaces but singly and doubly curved surface as well. It can be used for surfaces which are flat; singly curved such as cylindrically concave or convex, doubly convex, such as the surface of an egg; doubly concave, such as the inside surface of a spoon; or concavo-convex, such as the shape of a saddle-shaped surface. Another advantage of this technique for making a mold is that, although one goes through a multiple step process to make the mold, the mold can be repeatedly used, using rather low technology to produce bumps on the implants because the more complex technology is used to make the mold.

BRIEF DESCRIPTION OF THE DRAWINGS

The present invention and the objects achieved by it will be understood from the description of the preferred embodiments, taken in conjunction with the accompanying drawings of which.

DETAILED DESCRIPTION OF THE PREFERRED EMBODIMENTS

Figure 1A:
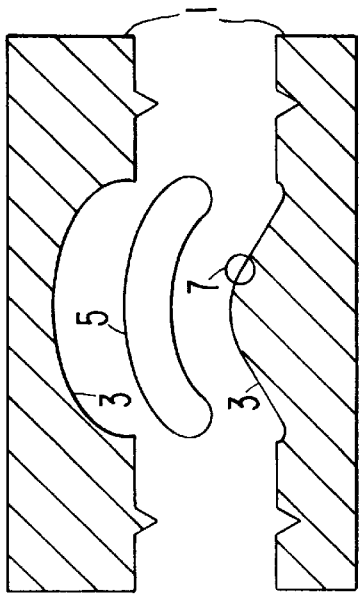
FIG. 1a is a cross-sectional view of a mold and a cast formed by the mold.

Reference will now be made in detail to the present preferred embodiments of the present invention, examples of which are illustrated in the accompanying drawings, wherein like reference numerals refer to like elements throughout.

The series of drawings from FIGS. 1a to 1j illustrate the sequence of steps for fabricating an implant with an implant surface having microscopic projections according to a preferred embodiment of the present invention. FIG. 1a shows a cross-sectional view of an epoxy mold 1 with a relatively smooth mold cavity surface 3. Mold 1 may also be made of other organic materials having a surface capable of being eroded by atomic oxygen bombardment. Mold 1 may be used to cast a solid elastomeric implant, to cast an elastomeric shell which is wrapped around a medical implant, or to cast an elastomeric shell or portion thereof which is placed, fused, or otherwise attached to a medical implant. Thus, the overall shape of the mold cavity surface 3 will depend upon the desired shape of the implant or the purpose for which a cast 5 is used. Moreover, depending on the purpose for which the cast 5 is used, surface roughness may be created on either or both sides of the cast 5. The method according to a preferred embodiment of the present invention also permits the creation of surface roughness in certain selected areas of the cast surface and the creation of surface roughness of a desired magnitude.

Figure 1B:
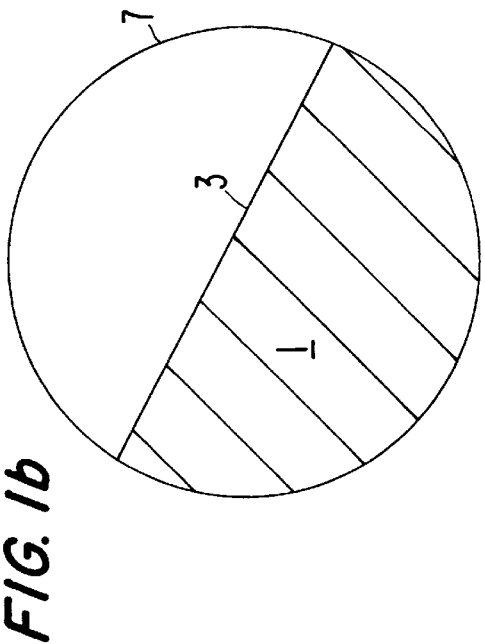
FIG. 1b is a cross-sectional view of the mold cavity surface.
Figure 1C:
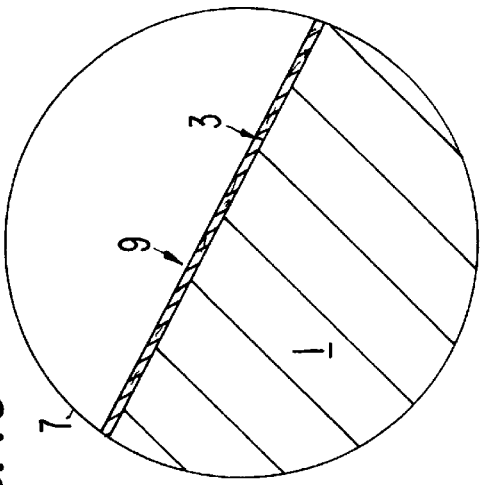
FIG. 1c is a cross-sectional view of the mold cavity surface with a controlled layer of fluid deposited upon it according to a preferred embodiment of the present invention.

The preparation of the mold cavity surface 3 according to a preferred embodiment of the present invention is described with reference to a blown up cross-sectional view 7 of the mold cavity surface 3, as shown in FIG. 1b. As shown in FIGS. 1a and 1b, the mold cavity surface 3 is initially relatively smooth. In one embodiment of the method of the present invention, a controlled layer of fluid 9 or solvent is initially created on the surface of the mold cavity 3, as shown in FIG 1c. The fluid may be water, an alcohol based mixture, or any volatile organic compound or adhesive that does not dissolve the mold material. In a preferred embodiment according to the invention, the controlled layer of fluid may be created by chilling the mold cavity surface 3 below the dew point so that a controlled layer of condensate, such as water vapor, will condense on the mold cavity surface 3. Spraying, brushing, or other methods well known in the industry for creating a controlled layer of fluid on a surface, may also be used.

Figure 1D:
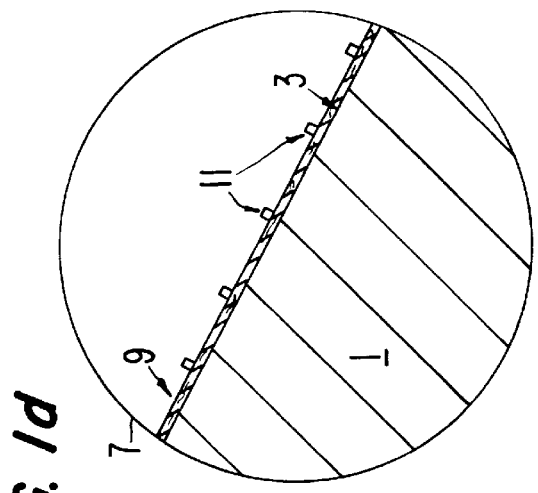
FIG. 1d is a cross-sectional view of the mold cavity surface with particles evenly distributed over the layer of fluid according to a preferred embodiment of the present invention.

Particles 11, such as salt crystals, capable of being attached to the mold cavity surface 3 by being partially dissolved by the controlled layer of fluid 9, are then distributed or dusted over the mold cavity surface 3. FIG. 1d shows an even distribution of such particles 11 on the mold cavity surface 3. Particles 11, including salt crystals other than sodium chloride crystals, may be used, as long as they can be removed as described below. The thin, controlled layer of fluid 9 or condensate is used to adhere particles 11 to the mold cavity surface 3. In other words, the layer of fluid 9 or condensate will cause the particles 11 to partially dissolve at the moisture interface such that the particles 11 become loosely attached to the mold cavity surface 3.

While FIG. 1d shows an even distribution of particles 11 on the mold cavity surface 3, other forms of distribution for the particles 11 are possible. The manner in which the particles 11 are distributed contributes to the magnitude and location of surface roughness on the cast 5. A relatively uniform distribution of particles 11 creates relatively uniform surface projections on the cast 5. The particles 11 may also be selectively distributed on portions of the mold cavity surface 3 to create surface roughness only in selected areas on the cast 5. Moreover, the amount of particles 11 concentrated in a particular area determines the magnitude of surface roughness in the corresponding area on the cast 5. In addition, the size and shape of the particles 11 and the extent to which the particles 11 dissolve also contribute to the magnitude of the resulting surface roughness on the cast 5.

After the particles 11 are distributed onto the mold cavity surface 3 and are allowed to partially dissolve, the fluid is removed without removing the particles 11 that are loosely attached to the mold cavity surface 3. The fluid may be removed by merely allowing it to evaporate. The removal of the fluid through evaporation may be expedited by heating.

Figure 1E:
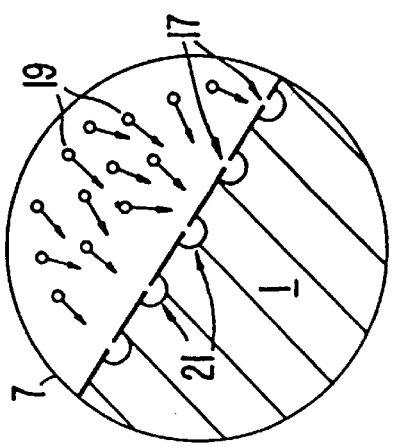
FIG. 1e is a cross-sectional view of the mold cavity surface having a thin film coating that was deposited over the mold cavity surface according to a preferred embodiment of the present invention.

As shown in FIG. 1e, a thin film coating 13 resistant to atomic particle bombardment, such as metals or metal oxides, is placed over the mold cavity surface 3 having the loosely attached particles 11. Various methods of applying the thin film coating, such as electron beam evaporation, hot filament evaporation, ion beam sputtering, magnatron sputtering, or any other evaporation or sputtering deposition techniques well known in the industry, may be employed. In a preferred embodiment of the method according to the present invention, aluminum is used for the thin film coating 13. The thin film coating 13 shields the mold cavity surface 3 from atomic particle bombardment later in the process.

Figure 1F:
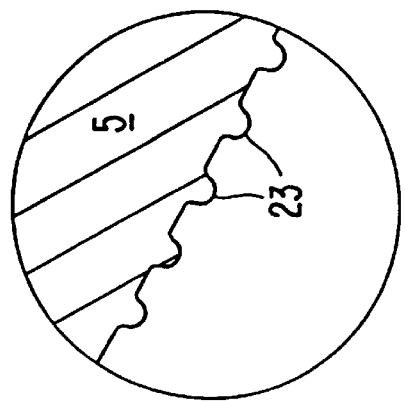
FIG. 1f is a cross-sectional view of the mold cavity surface having a thin film coating with pinholes created by the removal of the particles from the mold cavity surface according to a preferred embodiment of the present invention.

The metal coated particles 15 are then removed from the mold cavity surface 3 in order to create pinholes on the thin film coating 13 in the areas previously occupied by the particles 15. The particles 15 may be physically removed, such as by light brushing, or chemically removed by completely dissolving the particles 15 with water or another type of fluid not harmful to the mold. FIG. 1f shows the thin film 13 having pinholes 17 at the sites previously occupied by particles 15.

While the foregoing description of a preferred embodiment of the method according to the present invention employs a layer of fluid 3 and particles 11 in creating the pinholes 17 in the thin film coating 13, other methods of creating a thin film coating 13 having pinholes 17 are available. These other methods may be physical processes, such as puncturing the thin film coating 13 with sharp, pointed objects, or chemical processes, such as spraying a mist of an acidic compound over the thin film coating 13.

The mold cavity surface 3 with a thin film coating 13 having pinholes 17 is then subjected to atomic particle bombardment. In a preferred embodiment of the method according to the present invention, the mold cavity surface 3 is placed in a vacuum system and subjected to isotropic atomic oxygen bombardment. There are a variety of ways to achieve an isotropic atomic oxygen environment, such as by radio or microwave frequency plasma ashing, DC plasma ashing, or any other method well known in the industry for exciting oxygen or air plasma. In a preferred embodiment of the method of the present invention, radio frequency plasma ashing is employed, wherein the radio frequency plasma of air or oxygen is at a pressure of 50 to several hundred mtorr. Similarly, higher frequencies, such as microwave frequencies, may also be used to create an excited air or oxygen plasma. A DC plasma may also provide the necessary isotropic atomic oxygen environment.

Figure 1G:
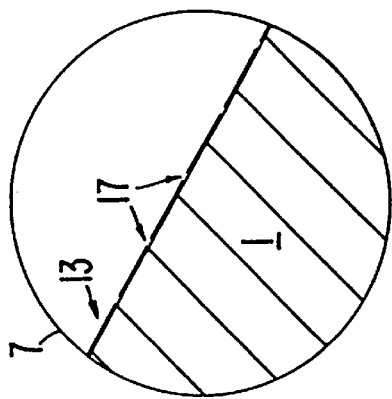
FIG. 1g is a cross-sectional view of the mold cavity surface with a thin film coating having pinholes, the mold cavity surface being bombarded with atomic particles according to a preferred embodiment of the present invention.

The atomic particle bombardment of the mold cavity surface 3 at the sites of the pinholes 17 creates microscopic near-hemispherical cavities or depressions on the mold cavity surface 3. FIG. 1g shows atomic particles 19 bombarding the mold cavity surface 3. The atomic particles 19 striking the pinhole sites oxidizes the mold cavity surface 3 underlying the thin film coating 13, creating cavities 21 in the mold cavity surface 3 at the location of the pinholes 17. Both the strength of the bombardment and the length of time that the mold cavity surface 3 is subjected to the atomic particle bombardment contribute to the magnitude of the resulting surface roughness on the cast 5 by affecting the size and shape of the cavities 21. Nevertheless, the cavities in the mold cavity surface 3 and the corresponding projections or bumps on the resulting cast are generally microscopic in size, ranging from less than 10 microns to several hundred microns.

Figure 1H:
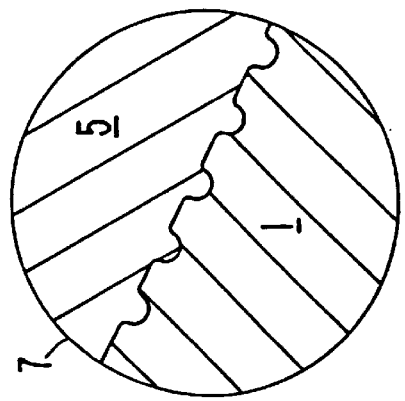
FIG. 1h is a cross-sectional view of the mold cavity surface having microscopic depressions created according to a preferred embodiment of the present invention.

After the depressions or cavities 21 in the mold cavity surface 3 are created from the atomic particle bombardment and oxidation, the atomic particle bombardment is stopped and the thin film coating 13 is removed. A sufficient mixture of acid, such as a dilute hydrochloric acid, may be used to remove the thin film coating 13. FIG. 1h shows the resulting mold cavity surface 3 after the thin film coating 13 is removed. The mold, now having depressions or cavities 21 on the mold cavity surface 3, is then used to cast an elastomeric medical implant, implant shell, or portion thereof.

Figure 1I:
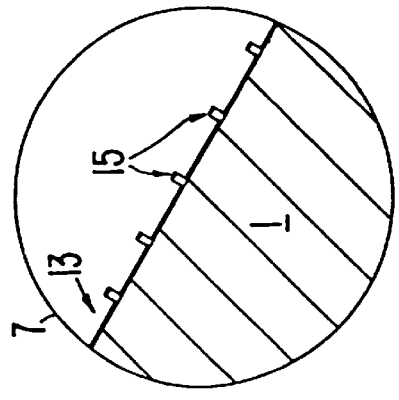
FIG. 1i is a cross-sectional view of the mold cavity surface with microscopic depression shaping the surface of a cast according to a preferred embodiment of the present invention.
Figure 1J:
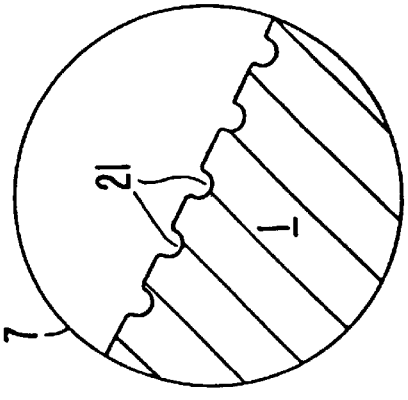
FIG. 1j is a cross-sectional view of the surface of a cast having microscopic bumps created according to a preferred embodiment of the present invention.

FIG. 1i shows the mold being used to form an elastomeric cast 5. The cast 5 may be made of silicone. A thin parting agent may also be applied during the molding step to assist in the separation of the cast from the mold. FIG. 1j shows the resulting external surface of the elastomeric cast 5 having microscopic projections or bumps 23. In addition to the creation of a rather uniform array of near-hemispherical projections as shown in FIG. 1j, other variations in surface morphology may be achieved depending on the manner in which the particles 11 were originally distributed, as discussed above.

Numerous modifications and adaptations of the present invention will be apparent to those skilled in the art. Thus, the following claims and their equivalents are intended to cover all such modifications and adaptations which fall within the true spirit and scope of the present invention.

What is claimed is:

1. A method for fabricating soft tissue implants having doubly curved or irregularly shaped surfaces, and having surface roughness from a mold made from an organic material, comprising the steps of:
   (a) coating a mold cavity surface of the mold with a thin film coating of material, which is resistant to atomic particle bombardment, and forming pinholes within said coating;
   (b) subjecting the mold cavity surface to atomic particle bombardment so that depressions are created in the mold cavity surface at the pinhole sites on the thin film coating;
   (c) removing the thin film coating from the mold cavity surface; and
   (d) creating an implant by using the mold to cast the implant.

2. A method as in claim 1, wherein said step (a) comprises the steps of:
   (a1) creating a controlled layer of fluid on the mold cavity surface;
   (a2) distributing particles, capable of being attached to the mold cavity surface by being partially dissolved by the fluid, onto the layer of fluid on the mold cavity surface;
   (a3) removing the fluid from the mold cavity surface without removing the particles that are attached to the mold cavity surface;
   (a4) applying a thin film coating, that is resistant to atomic particle bombardment, over the mold cavity surface; and
   (a5) removing the particles from the surface of the mold cavity so that pinholes are created at the sites on the thin film coating where the particles had occupied.

3. A method as in claim 2, wherein said step (a1) is carried out with water vapor.

4. A method as in claim 2, wherein said step (a1) is carried out with an organic adhesive.

5. A method as in claim 2, wherein said step (a1) comprises the steps of:

chilling the mold cavity surface below the dew point; and allowing a controlled layer of fluid to condense on the chilled mold cavity surface.

6. A method as in claim 2, wherein said step (a1) comprises the step of spraying a controlled layer of fluid onto the mold cavity surface.

7. A method as in claim 2, wherein said step (a1) comprises the step of brushing a controlled layer of fluid onto the mold cavity surface.

8. A method as in claim 2, wherein said step (a2) is carried out with particles of sodium chloride.

9. A method as in claim 2, wherein said step (a3) comprises the step of allowing the fluid to evaporate.

10. A method as in claim 2, wherein said step (a5) comprises the step of light brushing to remove the particles from the mold cavity surface.

11. A method as in claim 2, wherein said step (a5) comprises the step of fully dissolving the particles off the mold cavity surface.

12. A method as in claim 1, wherein said step (a) is carried out with a thin film coating of a metal or metal oxide.

13. A method as in claim 1, wherein said step (b) comprises the step of placing the mold in an isotropic atomic oxygen environment.

14. A method as in claim 1, wherein said step (d) further comprises the step of applying a thin parting agent to assist in the separation of the implant from the implant mold.

15. A mold for making soft tissue implants having doubly curved or irregularly shaped surfaces, and having a mold cavity surface treated in accordance with the method of (a) coating the mold cavity surface with a thin film coating of material, which is resistant to atomic particle, bombardment and forming pinholes within said coating;

(b) subjecting the mold cavity surface to atomic particle bombardment so that depressions are created in the mold cavity surface at the pinhole sites on the thin film coating; and (c) removing the thin film coating from the mold cavity surface.

16. A method for fabricating soft tissue implants having doubly curved or irregularly shaped surfaces, and having surface roughness from a mold made from an organic material, comprising the steps of:

(a) attaching particles to a mold cavity surface of the mold;

(b) coating the mold cavity surface with a thin film coating of material that is resistant to atomic particle bombardment;

(c) removing the particles from the coated mold cavity surface such that pinholes are created in the coating at the sites occupied by the particles;

(d) subjecting the mold cavity surface to atomic particle bombardment so that depressions are created in the mold cavity surface at the pinhole sites on the thin film coating;

(e) removing the thin film coating from the mold cavity surface; and (f) creating an implant by using the mold to cast the implant.

17. A method as in claim 16, wherein said step (a) comprises the steps of:

(a1) creating a controlled layer of fluid on the mold cavity surface;

(a2) distributing particles, capable of being attached to the mold cavity surface by being partially dissolved by the fluid, onto the layer of fluid on the mold cavity surface; and (a3) removing the fluid from the mold cavity surface without removing the particles that are attached to the mold cavity surface.

18. A method as in claim 17, wherein said step (a1) is carried out with water vapor.

19. A method as in claim 17, wherein said step (a1) is carried out with an organic adhesive.

20. A method as in claim 17, wherein said step (a1) comprises the steps of:

chilling the mold cavity surface below the dew point; and allowing a controlled layer of fluid to condense on the chilled mold cavity surface.

21. A method as in claim 17, wherein said step (a1) comprises the step of spraying a controlled layer of fluid onto the mold cavity surface.

22. A method as in claim 17, wherein said step (a1) comprises the step of brushing a controlled layer of fluid onto the mold cavity surface.

23. A method as in claim 17, wherein said step (a2) is carried out with particles of sodium chloride.

24. A method as in claim 17, wherein said step (a3) comprises the step of allowing the fluid to evaporate.

25. A method as in claim 16, wherein said step (b) is carried out with a thin film coating of a metal or metal oxide.

26. A method as in claim 16, wherein said step (c) comprises the step of light brushing to remove the particles from the mold cavity surface.

27. A method as in claim 16, wherein said step (c) comprises the step of fully dissolving the particles off the mold cavity surface.

28. A method as in claim 16, wherein said step (d) comprises the step of placing the mold in an isotropic atomic oxygen environment.

29. A method as in claim 16, wherein said step (f) further comprises the step of applying a thin parting agent to assist in the separation of the implant from the implant mold.

30. A mold for making soft tissue implants having doubly curved or irregularly shaped surfaces, and having a mold cavity surface treated in accordance with the method of:

(a) attaching particles to the mold cavity surface;

(b) coating the mold cavity surface with a thin film coating of material that is resistant to atomic particle bombardment;

(c) removing the particles from the coated mold cavity surface such that pinholes are created in the coating at the sites occupied by the particles;

(d) subjecting the mold cavity surface to atomic particle bombardment so that depressions are created in the mold cavity surface at the pinhole sites on the thin film coating; and (e) removing the thin film coating from the mold cavity surface.

\* \* \* \* \*